US007363928B2

(12) United States Patent
Shah

(10) Patent No.: US 7,363,928 B2
(45) Date of Patent: Apr. 29, 2008

(54) DILUTION RESISTANT VISCOELASTIC COMPOSITIONS

(75) Inventor: Mandar V. Shah, Rockaway, NJ (US)

(73) Assignee: Alcon, Inc., Hunenberg (CH)

( * ) Notice: Subject to any disclaimer, the term of this patent is extended or adjusted under 35 U.S.C. 154(b) by 324 days.

(21) Appl. No.: 10/882,923

(22) Filed: Jun. 30, 2004

(65) Prior Publication Data

US 2004/0241155 A1 Dec. 2, 2004

Related U.S. Application Data

(63) Continuation-in-part of application No. 10/380,135, filed as application No. PCT/US02/41247 on Dec. 20, 2002, now abandoned.

(60) Provisional application No. 60/342,916, filed on Dec. 21, 2001.

(51) Int. Cl.
*A61B 19/00* (2006.01)
*A61K 31/74* (2006.01)

(52) U.S. Cl. .................................. 128/898; 424/78.04
(58) Field of Classification Search ................ 128/898; 424/78.04
See application file for complete search history.

(56) References Cited

U.S. PATENT DOCUMENTS

| 4,328,803 A | 5/1982 | Pape |
| 4,443,432 A | 4/1984 | Garabedian et al. |
| 4,983,585 A | 1/1991 | Pennell et al. |
| 5,273,056 A | 12/1993 | McLaughlin et al. |
| 5,409,904 A * | 4/1995 | Hecht et al. ................... 514/23 |
| 5,498,606 A | 3/1996 | Harrison et al. |
| 5,627,162 A | 5/1997 | Gwon et al. |
| 5,792,103 A | 8/1998 | Schwartz et al. |
| 6,632,423 B2 | 10/2003 | Doshi et al. |
| 6,906,044 B2 | 6/2005 | Hermida Ochoa |
| 2004/0118414 A1 | 6/2004 | Shah |

FOREIGN PATENT DOCUMENTS

| EP | 0 136 782 | 4/1985 |
| JP | 2002-255829 A | 9/2002 |

OTHER PUBLICATIONS

Berson et al., "Obstruction of Aqueous Outflow by Sodium Hyaluronate in Enucleated Human Eyes, Am. J. Ophthalmology," vol. 95:668, 1983.

(Continued)

*Primary Examiner*—Thomas J Sweet
(74) *Attorney, Agent, or Firm*—Mark E. Flanigan

(57) ABSTRACT

A method of performing intra-articular therapy and a dilution resistant viscoelastic composition are disclosed. One embodiment of the dilution resistant composition comprises a hyaluronate-based viscoelastic agent and a low viscosity, polymer-containing solution. The hyaluronate-based viscoelastic can be an aqueous solution sodium hyaluronate having an average molecular weight greater than 750,000 Daltons and a concentration by weight between 0.5% and 3%. The polymer-containing solution can contain a polymer selected from the group consisting of chondroitin sulfate and hydroxypropylmethylcellulose. One embodiment can comprise a polymer-containing solution containing hydroxypropylmethylcellulose at a concentration by weight from about 0.05% to about 5.0% and chondroitin sulfate at a concentration by weight from about 0.1 to about 7%.

3 Claims, 2 Drawing Sheets

OTHER PUBLICATIONS

Fry, "Postoperative intraocular pressure rises: A comparison of Healon, Amvis, and Viscoat, J. Cataract Refractive Surgery," vol. 15:415, 1989.

Miyauchi eet al., "The Optimal Molecular Weight of Dispersive Type Sodium Hyaluronate for the Reduction of Corneal Endothelial Damage Induced by Sonication, Irrigation, and Aspiration," Jpn J. Ophthalmol., vol. 45:339-347, 2001.

Obstbaum, "Postoperative pressure evaluation. A rational approach to its prevention and management," J. Cataract Refractive Surgery, vol. 18:1, 992.

Olivius et al., "Intraocular pressure after cataract surgery with Healon®," Am. Intraocular Implant Soc. J., vol. 11:480, 1985.

Silver et al., "Physical Properties of Hyaluronic Acid and Hydroxypropylmethylcellulose in Solution: Evaluation of Coating Ability," J. Applied Biomaterials, vol. 5:89-98, 1994.

Arshinoff, S., Using the dispersive-cohesive viscoelastic soft-shell technique with different ophthalmic viscosurgical devices, Ophthalmic Practice, vol. 18(5):224-226, 2000.

Arshinoff, S., "The Ultimate Soft-shell Technique," Ophthalmic Practice, vol. 18(6):289-290, 2000.

Rainer, G., et al., Intraocular Pressure Rise After Small Incision Cataract Surgery: A Randomized Intraindividual Comparison Of Two Dispersive Viscoelastic England, Feb. 2001, vol. 85(2):139-142.

Holzer, M.P., et al., "Efect of Healon5 and 4 Other Viscoelastic Substances on Intraocular Pressure and Endothelium After Cataract Surgery." Journal of Cataract and Refractive Surgery, United States, Feb. 2001, vol. 27(2):213-218.

* cited by examiner

FIGURE 1/2
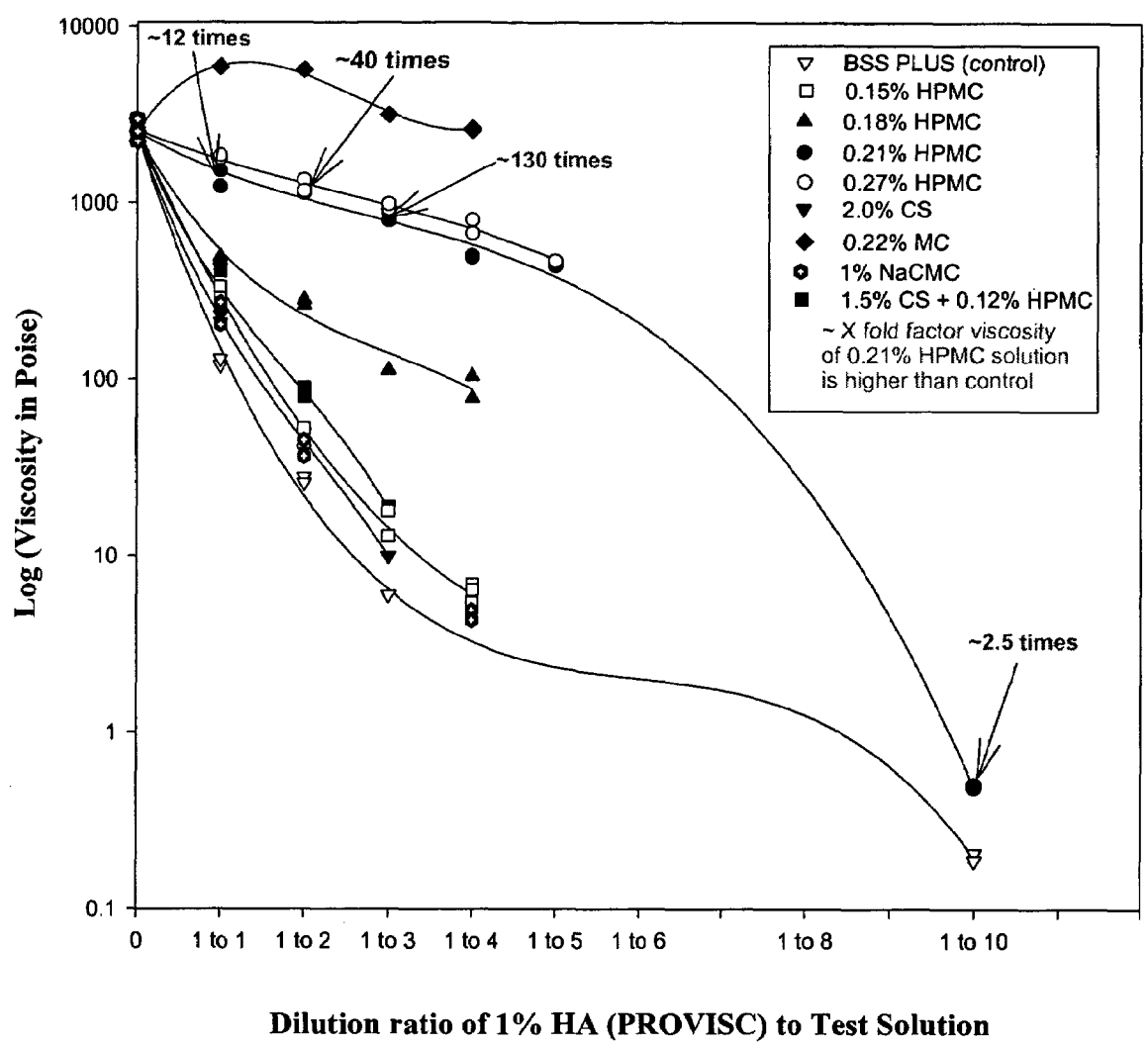

FIGURE 2/2
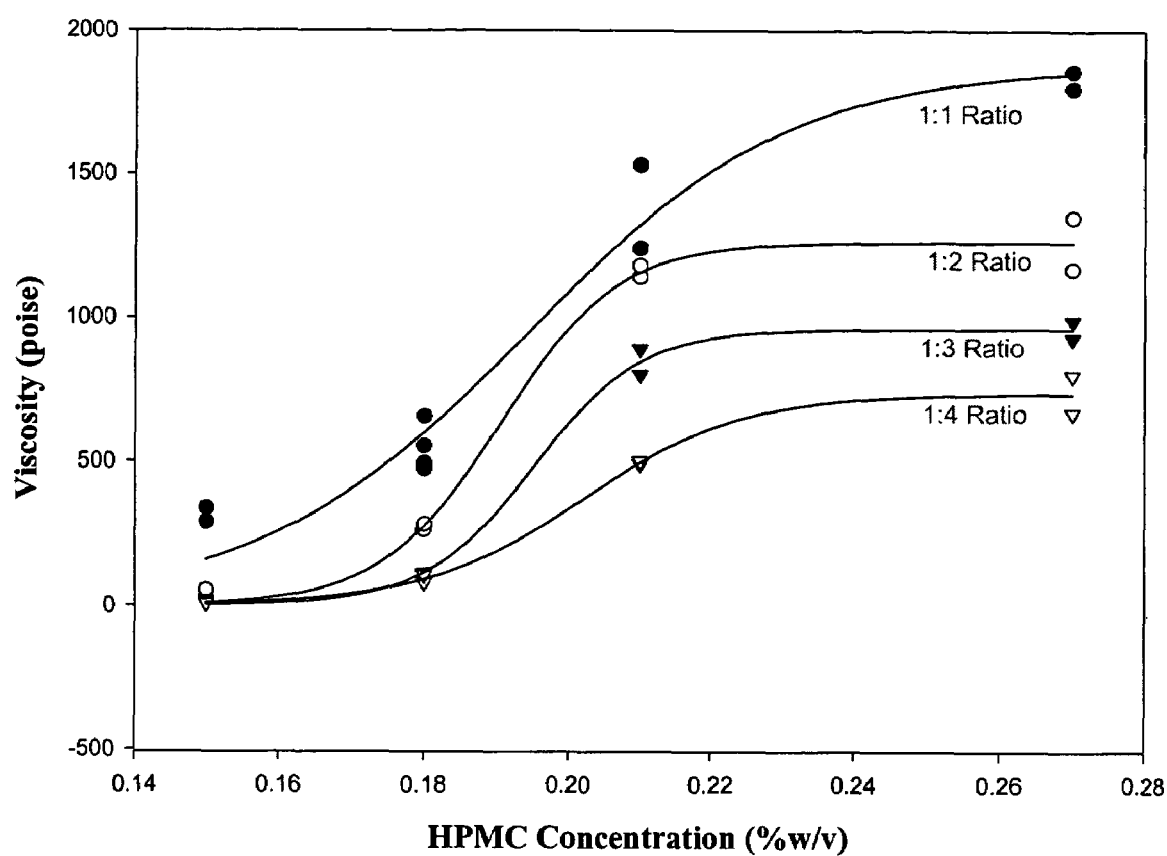

DILUTION RESISTANT VISCOELASTIC COMPOSITIONS

RELATED APPLICATIONS

The present application is a continuation-in-part application of U.S. patent application Ser. No. 10/380,135 filed Mar. 11, 2003 now abandoned, which is a national application under 35 U.S.C. § 371 of PCT Application Ser. No. PCT/US02/41247 filed Dec. 20, 2002, which draws priority from U.S. Provisional Application Ser. No. 60/342,916 filed Dec. 21, 2001, now abandoned.

TECHNICAL FIELD OF THE INVENTION

The present invention relates to novel viscoelastic compositions and their use in the field of surgery utilizing viscous and/or viscoelastic materials, also known as viscosurgery. In particular, the invention involves the combination of polymeric materials in aqueous solutions to enhance the performance of the viscosurgical materials, especially in certain environments. The invention also relates to methods of using such enhanced viscoelastic materials for all conventional purposes, and particularly those in which retention of the viscoelastic material is desirable, such as in intra-articular use and in certain ophthalmic surgical procedures.

BACKGROUND OF THE INVENTION

Viscous or viscoelastic agents used in surgery may perform a number of different functions, including, without limitation, maintenance and support of soft tissue, tissue manipulation, lubrication, tissue protection, and adhesion prevention. It is recognized that the differing rheological properties of these agents necessarily impact their ability to perform these functions, and, as a result, their suitability for certain surgical procedures. See, for example, U.S. Pat. No. 5,273,056, the contents of which are by this reference incorporated herein.

A number of viscous or viscoelastic agents (hereinafter "agents" or "viscoelastics") are known for ophthalmic surgical use: Viscoat® (Alcon Laboratories, Inc.) which contains sodium hyaluronate and chondroitin sulfate; Provisc® (Alcon), Healon®, Healon® GV, and Healon®5 (Pharmacia Corporation), Amvisc® and Amvisc® Plus (Bausch & Lomb, Inc.), and Vitrax® (Allergan Inc.) all of which contain sodium hyaluronate; and Cellugel® (Alcon) which contains hydroxypropylmethylcellulose (HPMC). All of the foregoing examples of viscoelastics may be used in cataract surgery. They are used by the skilled ophthalmic surgeon for several purposes, including maintenance of the anterior chamber of the eye and protection of ophthalmic tissues during surgery, particularly corneal endothelial cells, and as an aid in manipulating ophthalmic tissues.

While all of the agents described above may be used during cataract surgery, each has certain recognized advantages and disadvantages. Viscoelastics that are dispersive tend to offer better coating and protection of delicate tissues, such as the endothelial lining of the cornea. Cohesive viscoelastics, on the other hand, tend to be "stiffer", offering an advantage in soft tissue manipulation, e.g., capsulorhexis, but do not coat as well and are prone to accidental or premature aspiration. See, Miyauchi et al., "The Optimal Molecular Weight of Dispersive Type Sodium Hyaluronate for the Reduction of Corneal Endothelial Damage Induced by Sonication, Irrigation, and Aspiration," *Jpn J. Ophthalmol.*, 45:339-347 (2001). Thus, during phacoemulsification, a less cohesive, i.e. more dispersive, viscoelastic is desired to avoid total evacuation of the anterior chamber and collapse of the corneal dome. See also U.S. Pat. No. 5,273,056, which teaches sequential administration of viscoelastics possessing different rheological properties.

Generally, however, all such agents having sufficient viscosity and pseudoplasticity to be useful in ophthalmic surgery will, if left in the eye at the close of surgery, result in a transient increase in intraocular pressure ("IOP") known as an "IOP spike." (See, Obstbaum, *Postoperative pressure elevation. A rational approach to its prevention and management*, J. Cataract Refractive Surgery 18:1 (1992).) The pressure increase has been attributed to the agent's interference with the normal outflow of aqueous humor through the trabecular meshwork and Schlemm's canal. (See, Berson et al., *Obstruction of Aqueous Outflow by Sodium Hyaluronate in Enucleated Human Eyes*, Am. J. Ophthalmology, 95:668 (1983); Olivius et al., *Intraocular pressure after cataract surgery with Healon®*, Am. Intraocular Implant Soc. J. 11:480 (1985); Fry, *Postoperative intraocular pressure rises: A comparison of Healon, Amvis, and Viscoat*, J. Cataract Refractive Surgery 15:415 (1989).) IOP spikes, depending on their magnitude and duration, can cause significant and/or irreversible damage to susceptible ocular tissues, including, without limitation, the optic nerve.

Consequently, viscoelastics are typically removed from the eye just prior to the close of surgery. The ease with which an agent can be removed from the surgical site, typically by aspiration, has traditionally been considered an important characteristic in the overall assessment of the agent's usefulness in cataract surgery. By removing the agent before the close of surgery, the surgeon hopes to minimize or avoid any significant IOP spike. Unfortunately, however, removal of agents which are relatively dispersive (as opposed to cohesive) or which adhere to the ocular tissue is often difficult and may cause additional trauma to the eye.

Alternatives to removing the viscoelastic have been suggested. For example, exogenous dilution of the viscoelastic has been suggested to alleviate IOP spikes. See U.S. Pat. No. 4,328,803. Depending, however, on the particular viscoelastic and the surgical technique employed, IOP spike may still be a problem. More recently, it has been suggested that the administration of degradative agents to break down conventional viscoelastics in the eye can reduce or avoid the occurrence of IOP spikes. See, e.g., U.S. Pat. No. 5,792,103. Such an approach requires not only the administration of an enzymatic agent into the eye, the biocompatibility of which must be assured, but also means for adequately mixing the two agents via a special apparatus. Such approaches, which could leave residual material in the eye and thereby result in an IOP spike, have not been adopted by the ophthalmic community, which prefers to aspirate the viscoelastic from the eye at the close of surgery.

There is, therefore, a need for an improved means for reducing or avoiding IOP spikes associated with the use of conventional viscous or viscoelastic agents in ophthalmic surgery, especially cataract surgery. More specifically, a need exists for an improved methodology that will lend to traditional, hyaluronate-based viscoelastics variable rheological properties that can improve their performance during surgery and facilitate their removal at the end of surgery is recognized. The commonly assigned parent application to the present application, U.S. patent application Ser. No. 10/380,135, the entire contents of which are by this reference incorporated herein, is directed to an invention to serve this need. More specifically, that invention involves supplementing the irrigating solution used in such surgeries with relatively low molecular weight polymers that, when mixed with a cohesive hyaluronate-based viscoelastic, have the effect of modifying the rheological properties at the interface with the irrigating solution, and particularly the cohesiveness of such viscoelastic, to improve its performance in surgery. Irrigating solutions for use in surgery and particularly ophthalmic surgery are well known. See, e.g. commonly assigned U.S. Pat. No. 4,443,432. It has also been suggested that viscous or viscoelastomeric substances may be added to irrigating solutions to reduce cell loss. See commonly assigned U.S. Pat. No. 5,409,904, the contents of which are by this reference incorporated herein.

The use of viscoelastic agents in joint therapy is also known in the art. Viscoelastic joint therapy involves the intra-articular application of commercially available sodium hyaluronate viscoelastic materials such as HYLAN G-F 20, SYNVISC, HYALGAN, ARTZ, etc. The sodium hyaluronate substance is thought to affect the rheology of the synovial fluid, producing an almost immediate sensation of free movement and a marked reduction of pain in patients suffering from chondromalacia and/or arthritis, and particularly osteoarthritis. Chondroitin sulfate is also known to be useful in the treatment of diseased or traumatized joints. See U.S. Pat. No. 5,498,606. Viscoelastic materials such as sodium hyaluronate have also been used in cosmetic and reconstructive surgery to treat wrinkles and add fullness. Further, viscoelastic agents, for example sodium hyaluronate and chondroitin sulfate, have been used as a packing material for use in middle ear surgery, as described in commonly assigned U.S. Pat. No. 6,632,423, the contents of which are incorporated herein. However, for all applications in which sodium hyaluronate is subject to irrigation, whether exogenous or endogenous, there will be a dilution effect and a resulting loss of the desired viscosity, with a corresponding reduction in the time a treatment will remain effective (e.g., in reduction in pain viscoelastic joint therapy).

There is a need, therefore, for a viscoelastic substance that is less susceptible to dilution and viscosity loss than prior art viscoelastic substances.

SUMMARY OF THE INVENTION

The embodiments of the dilution resistant viscoelastic compositions of this invention substantially meet these needs and others. The present invention is directed to improved viscoelastic compositions for performing surgery, especially ophthalmic surgery, and for performing therapies, especially viscoelastic joint therapy, that require an increased resistance to dilution and loss of viscosity and/or varying rheological properties. Embodiments of this invention comprise viscous or viscoelastic agents in combination with an irrigating solution comprising a relatively low molecular weight polymer.

More specifically, the inventive methods of the embodiments of the present invention comprise transitioning the rheological properties (specifically viscosity and cohesiveness) of hyaluronate-based viscoelastic agents while also increasing their resistance to dilution and viscosity loss, by exposing such viscoelastic agents to irrigating solutions containing low levels of relatively low molecular weight biocompatible polymers, such as chondroitin sulfate ("CS"), and cellulosic polymers, especially methylcellulose ("MC") and hydroxypropylmethylcellulose ("HPMC"). The hyaluronate-based viscoelastic, at its interface with the polymer-containing irrigating solution, becomes less cohesive and, at the same time, more viscous. The decreased cohesiveness and increased viscosity of the surface hyaluronate interfacing the irrigating solution in situ renders it less susceptible to unintentional aspiration during a surgical procedure, such as cataract surgery. The hyaluronate material that is further removed from such surface (i.e. deeper within the bolus of material) retains its original lower viscosity and higher cohesiveness, and may therefore be readily aspirated at the conclusion of the surgery. In this manner, the skilled surgeon will be able to enjoy the positive aspects of different rheological profiles using the same hyaluronate-based material by modifying its properties with the polymer-containing irrigating solution to suit the particular phase of a surgery, i.e., capsulorhexis, phacoemulsification or aspiration of the viscoelastic.

A further aspect of the embodiments of this invention is especially applicable to therapies, such as viscoelastic joint therapy, that benefit from the ability of a viscoelastic composition to provide prolonged relief. This ability is directly related to the viscoelastic composition's dilution characteristics. By mixing such viscoelastic agents as described herein, the properties of the combined product are such that the resulting composition has an increased resistance to dilution whether by an exogenous or endogenous addition. Viscosity of the therapeutic agent can thus be maintained and its effectiveness prolonged.

BRIEF DESCRIPTION OF THE DRAWINGS

A more complete understanding of the present invention and the advantages thereof may be acquired by referring to the following description, taken in conjunction with the accompanying drawings in which like reference numbers indicate like features and wherein:

FIG. 1 shows the viscosity profile of various compositions of this invention plotted against the viscosity profiles of test solutions; and FIG. 2 illustrates zero shear viscosity at different HPMC concentrations and mixing ratios according to the teachings of this invention.

DETAILED DESCRIPTION OF THE PRESENT INVENTION

While particularly important in ophthalmic surgery, and especially cataract surgery, the methods and compositions of the present invention may be utilized in any viscosurgical procedure with a hyaluronate-based viscoelastic, and especially those in which there is concern over unintentional or premature removal of the viscoelastic material from the surgical site. In cataract surgery, the anterior chamber of the eye, i.e., the space between the iris and the corneal endothelium is filled with viscoelastic. The viscoelastic serves two purposes: (1) maintaining the corneal dome to give the surgeon an unobstructed view of the interior surgical site, and (2) protecting the delicate endothelial cells of the cornea by coating them. As discussed above, unsuccessful attempts have been made to find a viscoelastic material with a single, optimized rheology that achieves both of the foregoing objectives. Another approach has been to utilize separate cohesive and dispersive viscoelastic agents in the same surgical procedure. The DuoVisc® product marketed by Alcon Laboratories, Inc. utilizes this latter approach, and has enjoyed commercial success. Nevertheless, it would be preferable if the dual functions of the viscoelastic could be served by a single viscoelastic material. That objective is met using the methods and compositions of the present invention. The various embodiments of the viscoelastic compositions of this invention are also well suited for use as vitreous replacements in, for example, a vitreo-retinal surgery, and such use is contemplated to be within the scope of this invention.

Because of their ability to achieve enhanced retention times when injected into the body, the viscoelastic compositions of the present invention are also well-suited for joint therapy through intra-articular injection. The effect of conventional hyaluronate is temporary because the material remains within the articular chamber for only about 72 hours before it is absorbed and/or metabolized. The benefit of the longer retention times afforded by the compositions of the present invention is readily apparent, as the therapeutic effects of intra-articular viscotherapy with the compositions of the present invention should outlast those obtained with conventional viscoelastics. In a preferred embodiment, the compositions of the present invention for use in joint therapy will contain chondroitin sulfate, which is known to be particularly beneficial for human and animal joints. U.S. Pat. No. 5,498,606, the entire contents of which are by this reference incorporated herein, discloses the antiinflammatory and cell protective effects observed upon intra-articular injection of chondroitin sulfate in horse joints. More recently, it has been suggested that the intra-articular injection of VISCOAT, which contains a mixture of sodium hyaluronate and chondroitin sulfate, may cause cartilage regeneration in the joints of patients suffering from grade I and grade II osteoarthritis. In that regard, the contents of commonly assigned U.S. patent application Ser. No. 10/082, 743 are by this reference incorporated herein.

By using an irrigating solution that contains relatively low concentrations of lower molecular weight polymers such as HPMC, MC and CS, the rheology of a cohesive, hyaluronate-based viscoelastic material at the interface of the viscoelastic and the irrigating solution is significantly altered. The viscoelastic at such interface becomes less cohesive and more viscous, thereby minimizing inadvertent or premature aspiration and removal of the protective viscoelastic material from the eye. The term "hyaluronate-based viscoelastic" as used herein means any aqueous solution of hyaluronic acid or physiologically acceptable salts thereof, which is free of any significant amount of any low molecular weight, non-HA polymer. With the exception of Viscoat®, all of the commercial HA products described above are considered hyaluronate-based viscoelastics. As used herein, a "cohesive" hyaluronate-based viscoelastic would include any hyaluronate-based viscoelastic containing a hyaluronate component with a molecular weight of approximately 1,000,000 Daltons or more.

Lens removal surgery, such as cataract surgery, or the less common clear lensectomy, involves several different steps or phases. As previously discussed, differing rheological profiles may be preferred for the viscoelastic used in each of those steps or phases. For example, during capsulorhexis (opening of the capsular bag to expose the clear or cataractous lens), it is desirable to have a cohesive viscoelastic for space maintenance; during phacoemulsification (ultrasonic fragmentation of the lens) it is desirable to have a dispersive viscoelastic for better coating and maneuverability; finally, during artificial lens insertion and completion of the surgery, it is desirable to have a cohesive viscoelastic both for space maintenance and ease of removal. By using a polymer-containing irrigating solution, as described more fully below, with any of the conventional hyaluronate-based viscoelastic agents, one can, using the methods of the present invention, secure the preferred rheological profile at each step of the procedure.

One embodiment of the present invention comprises the following steps. A cohesive viscoelastic like PROVISC® (Alcon Laboratories, Inc., Fort Worth, Tex.), HEALON®, or HEALON GV®. (Pharmacia & Upjohn, Peapack, N.J.), or AMVISC® PLUS (Bausch & Lomb Surgical, Claremont, Calif.) is used before and during the capsulorhexis step. Immediately prior to commencing phacoemulsification, a small amount of polymer-containing irrigating solution is permitted to flow, without aspiration into the space separating the viscoelastic from the anterior surface of the exposed, typically cataractous lens. The phaco emulsification device is then engaged, without irrigation/aspiration, and the tip of the phaco emulsification handpiece is introduced into the surgical site and placed in the irrigating solution above the exposed lens. The ultrasonic waves from the tip of the phaco emulsification handpiece will promote the mixture of the irrigating solution and the viscoelastic agent at the interface of those two substances. This will change the cohesive property of the hyaluronate-based viscoelastic in the immediate vicinity of the lens rendering the viscoelastic more dispersive. After one to twenty seconds of mixing, the phacoemulsification of the lens, with irrigation/aspiration, is completed in the ordinary manner. At the end of surgery, the irrigation aspiration tip may be inserted into the bolus of viscoelastic material in the anterior chamber, i.e., beyond the more dispersive surface material at the interface and into the material not effected, or less effected, by admixture with the polymer-containing irrigating solution. The viscoelastic material in this region remains more cohesive and is therefore easily aspirated out with minimal effort and minimal trauma to the delicate endothelial cells.

The cohesive, hyaluronate viscoelastics suitable for use in the methods of the present invention include those commercial products identified above, which may generally be characterized as containing sodium hyaluronate (of course other physiologically acceptable hyaluronate salts could also be used) having average molecular weights greater than 500,000 Daltons, preferably from about 1,000,000 to about 5,000,000 Daltons, and concentrations from about 1.0 to about 3.0% by weight.

Irrigating solutions that may be used in the methods of the present invention include any sterile, aqueous irrigating solution suitable for surgery. Preferred are balanced salt solutions such as BSS® or BSS PLUS® (Alcon Laboratories, Inc., Fort Worth, Tex.). The addition of polymers to the irrigating solution may be effected in the manner described in U.S. Pat. No. 5,409,904, previously incorporated by reference. Preferred polymeric components for the irrigating solution include CS, MS and HPMC. The relatively low weight CS suitable for purposes of the present invention would include material having an average molecular weight of less than about 100,000 Daltons, preferably from about 20,000 to about 80,000 Daltons, and most preferably from about 30,000 to about 50,000. HPMC or MC used as the polymeric component of the irrigating solution in the present methods will have an average molecular weight below about 400,000 Daltons and, preferably from about 50,000 to about 200,000 Daltons, and most preferably from about 70,000 to about 100,000 Daltons. Concentration ranges for the polymeric components will vary depending upon the molecular weight of the polymeric component chosen, but should be maintained at levels low enough to retain the flow properties desired for an irrigating solution. For CS, the concentration in the irrigating solution may be from 0.1 to 10% by weight, preferably from 0.5 to about 7%, and most preferably from about 2% to about 5% by weight. For HPMC and MC, the concentration in the irrigating solution may be from 0.05 to 5%, preferably from about 0.1 to about 0.5%, and most preferably from about 0.2 to about 0.3%. Combinations of different low molecular weight polymers, as exemplified below, may also be used. For intra-articular use, the viscoelastic compositions of the present invention are mixed without an irrigation solution. The low molecular weight polymers are mixed with a hyaluronate-based viscoelastic, as discussed below, to achieve the properties described herein.

The following examples are provided to further illustrate various features of the present invention.

EXAMPLE 1

A 0.4 mL aliquost of PROVISC or VISCOAT, as the case may be is placed in a 5 mL reaction vial (conical interior, covered with a flat bottom). To the viscoelastic, 5 microliters of Na fluorescein solution (25% w/v) is added for visualization of the viscoelastic. 0.6 mL of appropriate irrigating solution is then added to the above vial, using a micropipette. The irrigating solution in contact with the viscoelastic is then agitated to promote partial mixing by engaging the ultrasound on the phacoemulsification handpiece tip, and placing such tip in the irrigating solution, (expression of additional irrigating solution should be avoided by lowering the irrigating solution bottle to a height below the level of the reaction vial). The ultrasound mixing is continued for 20 seconds, while moving the phaco tip, to mix the solution with the viscoelastic, along with the dye. After mixing, the height of the irrigating solution bottle is raised and irrigation/aspiration of the colored viscoelastic is commenced with ultrasound on. The time taken to fully aspirate the viscoelastic, working as efficiently and as quickly as possible, is recorded.

The above steps are repeated twice for each irrigating solution (i.e. a total of 3 runs) tested. The results for the various irrigating solutions are as shown below in Table 1.

TABLE 1

Aspiration Time for Various Irrigating Solutions/Viscoelastic Combinations

| BSS ®/ PROVISC | BSS ®/ VISCOAT | BSS PLUS ® PART I + 3.5% CS/PROVISC | BSS ® + 0.27% HPMC/PROVISC |
|---|---|---|---|
| 10 s | 29 s | 28 s | 31 s |
| 11 s | 30 s | 30 s | 32 s |
| 10 s | 29 s | 27 s | 31 s |
| Average: 10.3 s | 29.3 s | 28.3 | 31.3 s |

Discussion:

The above results demonstrate that PROVISC®, a cohesive viscoelastic, is aspirated very quickly, when regular BSS® is used in the irrigating solution. On the other hand, VISCOAT®, a well known dispersive viscoelastic, takes longer to aspirate. However, when CS or HPMC is in the irrigating solution, aspiration time of PROVISC® is closer to that of VISCOAT®, which indicates in situ changes in the physical properties of the hyaluronate-based viscoelastic.

It should be noted that the irrigating solution was mixed here with the help of ultrasound for 20 seconds, which was likely excessive. In actual surgery the mixing is only required at the interface of the irrigating solution and the viscoelastic, so the actual time needed may be 1 second or less, as the viscosity and cohesiveness of the viscoelastic changes almost instantly upon mixing.

EXAMPLE 2

TABLE 2

| Component | Amount (w/v %) | Function |
|---|---|---|
| HPMC [E4M from Dow Chemical] (Molecular weight: 86,000) | 0.1 to 0.3 | Rheology modifier |
| Sodium Chloride | 0.744 | Tonicity Agent |
| Potassium Chloride | 0.0395 | Essential Ion |
| Dibasic Sodium Phosphate (Anhydrous) | 0.0433 | Buffering Agent |
| Sodium Bicarbonate | 0.219% + 10 to 20% excess | Physiological Buffer |
| Hydrochloric Acid | Adjust Ph | Ph Adjust |
| Sodium Hydroxide | Adjust Ph | Ph Adjust |
| Water for Injection | 100% | Vehicle |

The formulation described in Table 2 above may be prepared as follows: First, the water for Injection is brought close to boiling or at boiling. The HPMC is then slowly added to the water under continuous stirring to thoroughly disperse it in the water. Then the mixture is slowly allowed to cool, stirring continuously. Once at room temperature, the mixture should start clearing up. The mixture is then stored overnight at 4° to 8° C. in an appropriate container to fully hydrate the HPMC. The following day, the remaining ingredients are added to the HPMC solution, pH of the solution is adjusted and additional water for injection is added if needed to bring the solution to final volume. The final solution is filtered, packaged in bottles and autoclaved.

EXAMPLE 3

TABLE 3

| Component | Amount (w/v %) | Function |
|---|---|---|
| MC [A15C Premium from Dow Chemical] (Molecular weight: 63,000) | 0.1 to 0.3 | Rheology modifier |
| Sodium Chloride | 0.744 | Tonicity Agent |
| Potassium Chloride | 0.0395 | Essential Ion |
| Dibasic Sodium Phosphate (Anhydrous) | 0.0433 | Buffering Agent |
| Sodium Bicarbonate | 0.219% + 10 to 20% excess | Physiological Buffer |
| Hydrochloric Acid | Adjust Ph | Ph Adjust |
| Sodium Hydroxide | Adjust Ph | Ph Adjust |
| Water for Injection | 100% | Vehicle |

The formulation described in Table 3 above may be prepared as follows: First, the water for Injection is brought close to boiling or at boiling. The MC is then slowly added to the water under continuous stirring to thoroughly disperse it in the water. Then the mixture is slowly allowed to cool, stirring continuously. Once at room temperature, the mixture should start clearing up. The mixture is then stored overnight at 4° to 8° C. in an appropriate container to fully hydrate the MC. The following day, the remaining ingredients are added to the MC solution, pH of the solution is adjusted and additional water for injection is added if needed to bring the solution to final volume. The final solution is filtered, packaged in bottles and autoclaved.

EXAMPLE 4

TABLE 4

| Component | Amount (w/v %) | Function |
| --- | --- | --- |
| CS (from Seikagaku) (Molecular weight: 40,000) | 2 to 5 | Rheology modifier |
| Sodium Chloride | 0.64 | Tonicity Agent |
| Potassium Chloride | 0.075 | Essential Ion |
| Calcium Chloride (Dihydrate) | 0.048 | Essential Ion |
| Magnesium Chloride (Hexahydrate) | 0.03 | Essential Ion |
| Sodium Acetate (Trihydrate) | 0.039 | Buffering Agent |
| Sodium Citrate (Dihydrate) | 0.17 | Buffering Agent |
| Hydrochloric Acid | Adjust pH | pH Adjust |
| Sodium Hydroxide | Adjust pH | pH Adjust |
| Water for Injection | 100% | Vehicle |

The formulation described in Table 4 above may be prepared as follows: First, the water for injection is allowed to cool to room temperature. The appropriate quantity of CS is slowly added to the water under continuous stirring to thoroughly disperse it in the water. Stirring continues until all CS is in solution. The remaining ingredients are then added sequentially to the CS solution, making sure that each such ingredient is dissolved before adding the next one. PH and volume of the solution are then adjusted. The final solution is sterile filtered and packaged in bottles. The solution may even be terminally sterilized by autoclaving.

The polymeric interaction of the HPMC, methylcellulose (MC), and chondroitin sulfate (CS) with the HA present in the viscoelastics discussed above provide useful rheological properties for use in ophthalmic surgery and intra-articular therapy. HPMC, MC and CS have a strong polymeric interaction with HA. The polymers have some basic difference in their interaction, resulting in different physical properties. When HPMC and MC interact with HA, there is a large impact on viscosity. On the other hand, CS appears to have less of an impact on the resultant viscosity. HPMC and MC both make the mixture more dispersive than the control (BSS PLUS®). However, this dispersiveness may be due to the fact that HPMC and MC are surface active polymers, which means they reduce the surface tension of the mixture, thus making the mixture more dispersive.

The interaction of MC with HA is much stronger than that of HPMC with HA. In fact the interaction of MC and HA is so strong that the resultant increase in viscosity overcomes the dilution effect. An important aspect of the interaction of MC and HPMC with HA is that the resultant viscosity in both the cases is resistant to dilution. This property has applications beyond use of these polymers in an irrigating solution, such as for intra-articular therapy.

Concentration dependence on the interaction with HA was studied for HPMC. The result is a sigmoid shaped plot where increase in the resultant viscosity is initially small, when HPMC concentration is increased up to 0.18%. However, increasing the HPMC concentration to 0.21% causes a large increase in viscosity, which appears to level off when the HPMC concentration is further increased. These results are illustrated in FIG. 2, discussed in more detail below.

During a typical ophthalmic surgery, such as phacoemulsification to remove a cataract, irrigating solution is infused, which continuously dilutes the viscoelastic. The effects of diluting various viscoelastic agents using an irrigation solution comprising various ratios of the cellulosic polymers discussed herein were studied and the resultant viscosity was determined. The methodology used and results obtained are summarized below.

EXAMPLE 5

Sample Preparation for Determination of Viscosity

The plunger was removed from a 10 mL sterile plastic syringe and the other end closed off with a sterile tip cap. The syringe was placed upright in a beaker on a balance. PROVISC was transferred into the syringe by weight. Using another syringe in a similar fashion, test irrigating solution was also transferred by weight.

Following the addition of PROVISC and the test irrigating solution into the syringe, the plunger was carefully placed back into each individual syringe, the tip cap was removed and a luer connector was attached to one of the syringes. The other syringe was attached to the other end of the luer connector. The contents were then thoroughly mixed by alternately pushing plungers of the conjoined syringes for 2 minutes.

The actual amount of PROVISC and test solution varied, depending on the intended ratio of the two materials. For viscosity determination, 4 g of total material was needed. The test solutions were BSS PLUS® (control); BSS PLUS® with varying concentrations of HPMC; BSS PLUS® containing 2% chondroitin sulfate (CS); BSS PLUS® containing 1% sodium carboxymethylcellulose (NaCMC); and (BSS PLUS® with 0.22% methylcellulose (MC). The weight of PROVISC to that of the test solution was adjusted such that it was in a 1:1, 1:2, 1:3, 1:4, 1:5 or 1:10 ratio for viscosity determination. The concentrations of MC, CS and NaCMC were chosen such that they would provide a viscosity of 4.0 cps at 25° C.

After hand mixing of PROVISC and the test solution, the mix was sonicated for 30 seconds, followed by further hand mixing in the conjoined syringes for five additional passes. Contents were then transferred into a centrifuge tube. The centrifuge tube was labeled and then spun for 2 minutes at low speed of 2500 rpm to remove air bubbles. The sample was allowed to sit overnight in a refrigerator. The rheological profile of the product (viscosity) was determined on the following day.

Determination of Rheological Profile (Zero Shear Viscosity)

The Theological profile was determined by using a Bohlin CS Rheometer. A 4° cone and 40 mm diameter plate (CP 4/40) at a gap width of 0.15 mm was used. Viscosity was determined at 25° C. Shear stresses applied were from 0.06 to 139 Pa. The corresponding shear rate and viscosity was calculated by the Bohlin software after 200 seconds of integration or whenever the system approved steady state was reached.

Viscosity Results

Based on the applied shear stress, the Bohlin CS Rheometer calculates the shear rate and apparent viscosity at that shear rate. The logarithm of viscosity in Pascal seconds (Pas) is plotted on the Y-axis against the corresponding shear rate in reciprocal seconds (1/s) on the X-axis. Usually, for most viscoelastics, there is a significant plateau for viscosity, at low shear rates. The extent of the plateau varies with different viscoelastics. The intercept of the plateau on the Y-axis is considered as zero shear viscosity. When the shear rate is increased further, viscosity drops exponentially.

Similar to most viscoelastics, the viscosity profile of PROVISC alone or PROVISC diluted to various ratios with BSS PLUS® exhibited a typical plateau. However, when PROVISC was diluted with an irrigating solution containing HPMC or MC the characteristic plateau was not always present. Instead, some fluctuation in viscosity was observed. This behavior was more pronounced as the concentration of HPMC increased. To determine the zero shear viscosity, average viscosity between the shear rate of $1 \times 10^{-3}$ to $9.9 \times 10^{-3}$ per second was calculated. Occasionally shear rates up to $5 \times 10^{-2}$ per second were necessary to perform the average viscosity calculation. The average zero shear viscosities of the different mixtures are presented in Table 5 below and the data are plotted in FIG. 1.

TABLE 5

Zero Shear Viscosity of Various Mixtures of Irrigating Solution with Provisc at Different Ratios
For the different ratios, proportional weight of PROVISC was always kept at 1, while that of the irrigating solution was increased up to 10. The various additives listed in the column of Product Name were added to BSS PLUS ® part I. Various mixtures listed here were prepared by the methods discussed above.

Zero Shear Viscosity* of PROVISC and other Solutions mixed in different ratios.
All viscosities are in poise

| Product Name | 1:1 ratio | 1:2 ratio | 1:3 ratio | 1:4 ratio | 1:5 ratio | 1:10 ratio |
|---|---|---|---|---|---|---|
| PROVISC (undiluted) (For comparison) | 2240 2540 2990 | 2240 2540 2990 | 2240 2540 2990 | 2240 2540 2990 | 2240 2540 2990 | 2240 2540 2990 |
| PROVISC + BSS PLUS ® (control) | 120 130 | 28 26 | 6.0 6.0 | — | — | 0.21 0.17 0.19 |
| PROVISC + 0.15% HPMC | 288 336 | 44 53 | 18 13 | 5.4 5.4 6.9 6.4 | — | — |
| PROVISC + 0.18% HPMC | 473 493 655 553 | 263 282 | 113 | 78 104 | — | — |
| PROVISC + 0.21% HPMC | 1530 1240 | 1140 1180 | 800 890 | 490 500 | 440 | 0.5 0.49 |
| PROVISC + 0.27% HPMC | 1800 1860 | 1350 1170 | 990 930 | 670 800 | 470 | — |
| PROVISC + 0.22% Methyl-Cellulose | 5930 5980 | 5720 | 3187 | 2580 2654 | — | — |
| PROVISC + 1.0% NaCMC | 272 203 | 45 37 | — | 4.9 4.3 | — | — |
| PROVISC + 1.5% CS + 0.12 % HPMC | 260 410 | 80 130 90 | 18 25 19 | — | — | — |
| PROVISC + 2.0% CS | 230 210 | 40 50 | 10 10 | — | — | — |

*Zero Shear Viscosity for solutions, was determined by taking average of the viscosities at shear rate of $1 \times 10^{-3}$ to $9.9 \times 10^{-3}$ per second whenever a clear plateau was not available.

As seen from Table 5, upon dilution of PROVISC with BSS PLUS® in a 1:1, 1:2 or 1:3 ratio, the resultant viscosity dropped exponentially. PROVISC and BSS PLUS® mixture, without addition of HPMC or MC, served as a control at each dilution.

When 2% CS was present in the solution, the viscosity drop upon dilution was less than that observed with the BSS PLUS® control. When 2% CS was present in the solution, the resultant viscosity was almost twice that of the control. This indicates that there is some interaction between CS and HA, consistent with the previous experience of VISCOAT.

When the irrigating solution contained 0.21% or more HPMC, the viscosity drop upon dilution was much less than observed with the BSS PLUS® control. At 1:1 dilution, the resultant viscosity was 12 times higher than control; at 1:2 dilution it was 40 times higher than control; and at 1:3 dilution, it was 130 times higher than control. This behavior is indicative of the HA interaction with HPMC. The resultant composition is resistant to dilution, as illustrated graphically in FIG. 1.

In FIG. 2, zero shear viscosity at different HPMC concentrations and mixing ratios are plotted using the data from Table 5. HA concentration remained constant in all plots. The graphs are sigmoid shaped, indicating that increasing HPMC concentration above a critical value of 0.18% causes a substantial jump in the viscosity of the mixture. In the range of 0.21 to 0.27% HPMC, viscosity leveled off.

MC was tested only at a concentration of 0.22% and NaCMC was tested only at 1%. MC showed strong interaction with HA to the point that it overcame the effect of dilution, with the resultant viscosity even higher than that of PROVISC (Table 4). In strong contrast, NaCMC showed little interaction with HA, being only slightly higher than the control and substantially less than HPMC or MC, based on the viscosity data. Structurally, HPMC, NaCMC and MC have different substituents on anhydroglucose units of natural cellulose at the same site on the molecule. MC has a methyl group, HPMC has hydroxypropyl group and NaCMC has a sodium carboxymethyl group. Since we observe such wide changes in viscosity with different substituents on this site, this site may be responsible for the interaction. MC and HPMC have one additional methyl group on the opposite side, which is absent for NaCMC. Additionally, NaCMC is an ionic polymer, unlike HPMC and MC.

As can be seen from the above, HPMC, MC and CS appear to have a strong interaction with HA while NaCMC appears to have a weak interaction with HA, if any. There appears to be some basic difference in the interaction to the different polymers, resulting in different physical properties of the different compositions. When HPMC and MC interact with HA, there is a large impact on viscosity. HPMC and MC are both surface active polymers, so they reduce surface tension of the mixture and thus make the mixture more dispersive. Surface tension of various solutions are listed in Table 6 below.

Between HPMC and MC, interaction of MC with HA is much stronger. The interaction of MC and HA is so strong that the resultant increase in viscosity overcomes the dilution effect to a greater extent then when combining HPMC with HA. The important aspect about the interaction of MC and HPMC with HA is that the resultant viscosity in both cases is resistant to dilution. This property of the resulting compositions has important applications, as disclosed herein, within various fields, and in particular, for ophthalmic surgery and for intra-articular therapy.

TABLE 6

Surface tension of the Test Irrigating Solution at 25° C.

| Test Irrigating Solution | Surface Tension (dynes/cm) | | |
|---|---|---|---|
| | I | II | Average |
| Purified Water | 72.297 | — | 72.297 |
| BSS PLUS ® Part I | 72.900 | 72.831 | 72.866 |
| BSS PLUS ® Part I with 0.15% HPMC | 47.909 | 47.768 | 47.839 |
| BSS PLUS ® Part I with 0.21% HPMC | 47.960 | 47.348 | 47.654 |
| BSS PLUS ® Part I with 0.27% HPMC | 47.393 | 46.823 | 47.108 |
| BSS PLUS ® Part I with 0.22% MC | 49.954 | 50.161 | 50.058 |
| BSS PLUS ® Part I with 1.0% NaCMC | 72.456 | 72.859 | 72.658 |
| BSS PLUS ® Part I with 2.0% CS | 71.245 | 71.339 | 71.292 |

The present invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims.

What is claimed:

1. A method of performing intra-articular therapy comprising:
    introducing a dilution resistant viscoelastic composition into the site of the intra-articular therapy, wherein the dilution resistant viscoelastic composition comprises:
        a hyaluronate-based viscoelastic agent, wherein the hyaluronate-based viscoelastic is an aqueous solution sodium hyaluronate having an average molecular weight greater than 750,000 Daltons and a concentration by weight between 0.5% and 3%; and
        a low viscosity polymer, wherein the polymer is selected from the group consisting of methylcellulose, hydroxypropylmethylcellulose, and combinations thereof, and wherein said polymer is present at a concentration of at least about 0.2% by weight.

2. The method of claim 1, wherein the polymer comprises hydroxypropylmethylcellulose or methylcellulose at a concentration by weight from about 0.2% to about 5.0%.

3. The method of claim 2, wherein the concentration of the hydroxypropylmethylcellulose or methylcellulose is about 0.2 to 0.3% by weight and has an average molecular weight of about 80,000 Daltons.

* * * * *